US00PP09688P

United States Patent [19]

Olesen et al.

[11] Patent Number: Plant 9,688

[45] Date of Patent: Nov. 12, 1996

[54] FLORIBUNDA ROSE PLANT NAMED 'POULREK'

[75] Inventors: Mogens N. Olesen; Pernille Olesen, both of Fredensborg, Denmark

[73] Assignee: Bear Creek Gardens, Inc., Medford, Oreg.

[21] Appl. No.: 588,820

[22] Filed: Jan. 19, 1996

[51] Int. Cl.[6] ..... A01H 5/00

[52] U.S. Cl. ..... Plt./26

[58] Field of Search ..... Plt./22, 26, 24

*Primary Examiner*—Howard J. Locker

*Attorney, Agent, or Firm*—Klarquist Sparkman Campbell Leigh & Whinston, LLP

[57] ABSTRACT

A repeat flowering floribunda having a very even compact growth habit, glossy dark green foilage, rapid repeat flowering with new shoots forced behind the terminal flower to produce constant bloom, resistance to rose powdery mildew and rust, and readily propagated by budding or soft wood cuttings.

1 Drawing Sheet

The present invention relates to a new and distinct variety of rose plant of the floribunda class which was originated by out crossing the variety MACrexy, U.S. Plant Pat. No. 6713, with an unnamed seedling.

The primary objective of this breeding was to produce a new rose variety having the compact free flowering characteristic of the female parent combined with the compact plant habit, even growth, rapid repeat bloom and resistance against fungal diseases of the male parent. The objective was substantially achieved, along with other desirable improvements, as evidenced by the following unique combination of characteristics that are outstanding in the new variety and that distinguish it from its parents, as well as from all other varieties of which we are aware:

1. A very even compact growth habit;
2. Glossy dark green foliage;
3. Rapid repeat flowering with new shoots forced behind the terminal flower to ensure constant bloom;
4. Ease of propagation by budding or soft wood cuttings; and
5. Resistance to rose powdery mildew and rust.

Asexual reproduction of this new variety by budding and by softwood cuttings, as performed at Wasco, Calif. and Fredensborg, Denmark, shows that the foregoing characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in a color illustration of this character.

The following is a detailed description of our new rose cultivar with color descriptions using terminology in accordance with The Royal Horticultural Society (London) Colour Chart, except where ordinary dictionary significance of color is indicated.

Parentage:

*Seed parent.*—MACrexy.

*Pollen parent.*—Unnamed seedling.

Classification:

*Botanical.*—Rosa hybrida.

*Commercial.*—Floribunda.

FLOWER

Observations made from specimens grown in a garden environment in Somis, Calif., in March through November, 1995.

Blooming habit: Continuous.

Bud:

*Size.*—1 inch long when the petals start to unfurl.

*Form.*—Long, pointed ovoid.

*Color.*—When sepals first divide, bud color is Red Group 36C on the upper ¼ of the dividing bud petals. The rest of the bud is Yellow-Orange Group 23C. When half blown, the upper sides of the petals are Red Group 36D; and the lower sides of the petals are Red Group 36D.

*Sepals.*—Color: Green Group 138B. Surface texture: Covered in fine hairs. There are three lightly appendaged sepals. There are two unappendaged sepals with hairy edges.

*Receptacle.*—Color: Green Group 137D. Shape: Funnel. Size: Small (3/16"×¼"). Surface: Smooth.

*Peduncle.*—Length: Short (2½"). Surface: Smooth with some very small glands. Color: Medium green. Strength: Stiff, slender.

Bloom:

*Size.*—Medium. Average open size is 3½"–3¾".

*Borne.*—Singly and several together in rounded clusters.

*Stems.*—Short, strong ( about 8 to 10 inches).

*Form.*—When first open: High center. Permanence: Flattens, outer petals curl back.

*Petalage.*—Number of petals under normal conditions: 30.

*Color.*—The upper side of the petals is Red Group 36D except near the base of the petal where it is Yellow Group 4D. The reverse side of the petals is Red Group 36D except near the base of the petal where it is Yellow Group 4D. The color of the base of petals is Yellow Group 4D. The major color on the upper side is Red Group 36D.

*Variegations.*—None.

*Discoloration.*—No general tonality change at the end of the first day. A fading of the very pale pink color to near white is observed at the end of the third day. Petals drop cleanly by day 5.

*Fragrance.*—Slight.

Petals:

*Texture.*—Thin.

*Shape.*—Obovate.

*Form.*—Tips slightly recurved, edges slightly quilled.

*Arrangement.*—Imbricated, with many large petaloids in the center.

*Persistence.*—Drop off cleanly.

*Lastingness.*—On the plant: Fair, 4–5 days. As a cut flower: Not tested.

Reproductive parts:

*Anthers.*—Size: Medium. Quantity: Few. Color: Yellow. Arrangement: Regular around styles, mixed with petaloids.

*Filaments.*—Color: Yellow.

*Pollen.*—Color: Gold Yellow.

*Styles.*—Color: Red.

*Stigmas.*—Color: Greenish white.

Form: Bush.

Growth: Vigorous, upright and spreading, branching. Height unpruned after one year of growth; 36"–42"; width unpruned after one year of growth; 24"–30".

Foliage:

*Size.*—Medium (4"33 2½").

*Quantity.*—Abundant.

*Color.*—New foliage: Some anthocyanin present — Greyed Orange 176B on both upper and lower. Old foliage: Upper: Green Group 139A. Lower: Green Group 137C.

Leaflets:

*Number.*—5 or occasionally 7.

*Shape.*—Broadly oval.

*Texture.*—Upper side: Leathery, glossy.

*Edge.*—Serrated.

*Serration.*—Single, small.

*Petiole rachis color.*—Green.

*Petiole underside.*—Smooth with some prickles.

*Stipules.*—Short (½"), serrated, bearded.

*Disease resistance.*—Resistant to mildew and rust under normal growing conditions at Somis, Calif.

Wood:

*New wood.*—Color: Light Green. Bark: Smooth.

*Old wood.*—Color: Green. Bark: Smooth.

Prickles:

*Quantity.*—On main canes from base: Ordinary. On laterals from main canes: Ordinary.

*Form.*—Short (¼"), straight.

*Color when young.*—Red.

Small prickles:

*Quantity.*—On main stalks: None. On laterals: None.

We claim:

1. A new and distinct variety of rose plant of the floribunda class, substantially as herein shown and described, characterized particularly as to novelty by the unique combination of its very even compact growth; its rapid repeat bloom; its resistance to powdery mildew and rust; its dark green glossy foliage; and its ease of propagation by budding and by softwood cuttings.

* * * * *

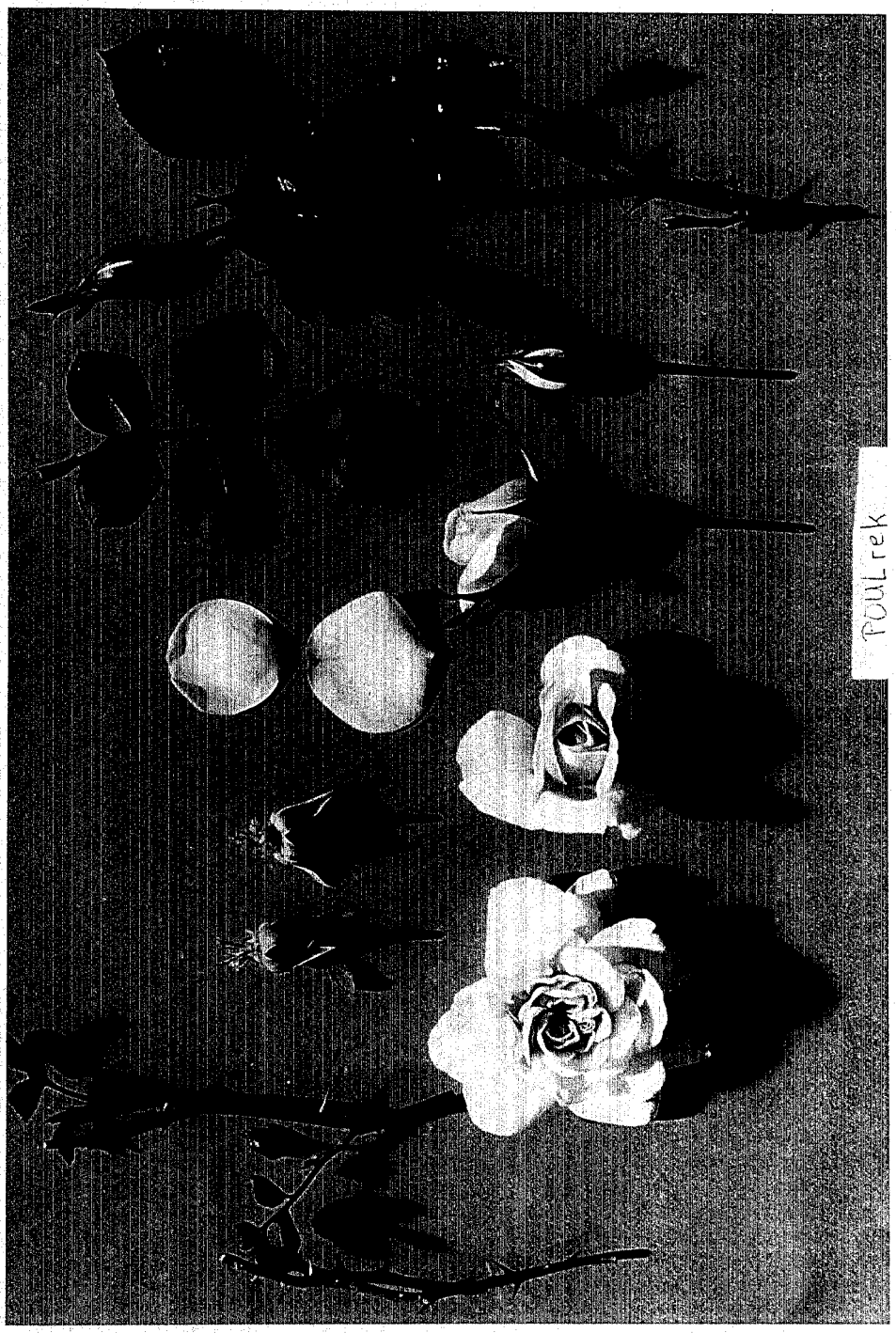
POUL rek